(12) United States Patent
Lo et al.

(10) Patent No.: US 10,232,161 B2
(45) Date of Patent: Mar. 19, 2019

(54) ULTRASONIC DEVICE FOR TRANSVERSELY MANIPULATING DRUG DELIVERY CARRIERS AND METHOD USING THE SAME

(71) Applicant: NATIONAL TSING HUA UNIVERSITY, Hsinchu (TW)

(72) Inventors: Wei-Chen Lo, Hualien County (TW); Chih-Kuang Yeh, Hsinchu (TW); Shih-Tsung Kang, New Taipei (TW); Zong-Han Hsieh, Taichung (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 102 days.

(21) Appl. No.: 15/263,387

(22) Filed: Sep. 13, 2016

(65) Prior Publication Data

US 2018/0071505 A1 Mar. 15, 2018

(51) Int. Cl.
| | | |
|---|---|---|
| *A61K 9/00* | (2006.01) | |
| *A61N 7/00* | (2006.01) | |
| *A61K 41/00* | (2006.01) | |
| *A61M 37/00* | (2006.01) | |

(52) U.S. Cl.
CPC ....... *A61M 37/0092* (2013.01); *A61K 9/0009* (2013.01); *A61K 41/0028* (2013.01); *A61N 7/00* (2013.01)

(58) Field of Classification Search
CPC ...... A61M 37/0092; A61M 2037/0007; A61K 9/0009; A61K 41/0028; A61N 7/00
See application file for complete search history.

(56) References Cited

U.S. PATENT DOCUMENTS

| | | | |
|---|---|---|---|
| 6,029,518 A | 2/2000 | Oeftering | |
| 2008/0294073 A1* | 11/2008 | Barthe | A61N 7/02 601/3 |
| 2008/0319356 A1* | 12/2008 | Cain | A61B 17/22004 601/2 |
| 2013/0046229 A1 | 2/2013 | Konofagou et al. | |
| 2013/0261442 A1* | 10/2013 | Yang | A61M 37/0092 600/431 |
| 2014/0276367 A1* | 9/2014 | Kersten | A61M 37/0092 604/22 |
| 2015/0105658 A1* | 4/2015 | Park | A61B 8/481 600/431 |
| 2015/0272601 A1* | 10/2015 | Dixon | A61B 17/2202 604/22 |
| 2016/0250457 A1* | 9/2016 | Bock | A61M 37/0092 604/22 |
| 2017/0360460 A9* | 12/2017 | Dixon | A61B 17/2202 |

FOREIGN PATENT DOCUMENTS

WO 2013140175 A1 9/2013

* cited by examiner

*Primary Examiner* — Lauren P Farrar
(74) *Attorney, Agent, or Firm* — CKC & Partners Co., LLC

(57) ABSTRACT

An ultrasonic device for transversely manipulating drug delivery carriers includes a driving unit and a transducer. The transducer is electrically connected to the driving unit and has a piezoelectric sheet in a curved shape. The piezoelectric sheet includes a plurality of channels, and a phase difference is generated between every two of the channels by the driving unit for producing an acoustic vortex.

15 Claims, 11 Drawing Sheets
(6 of 11 Drawing Sheet(s) Filed in Color)

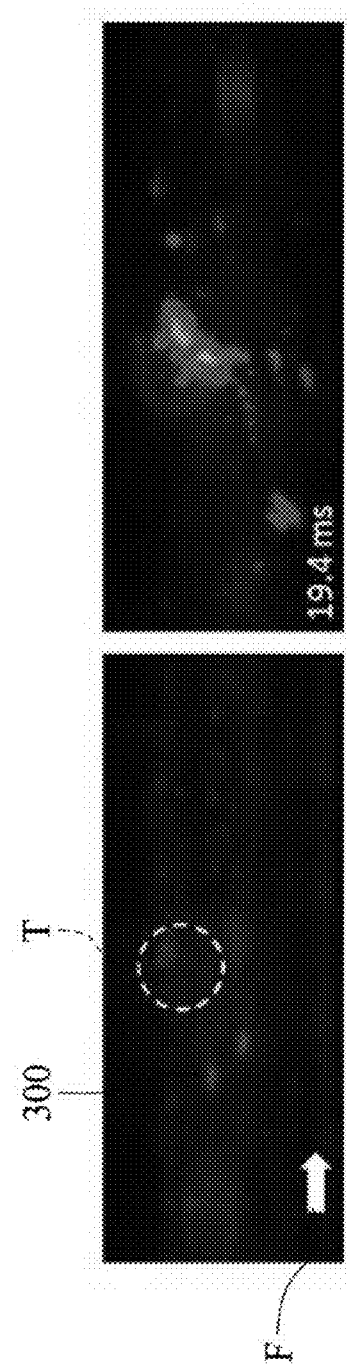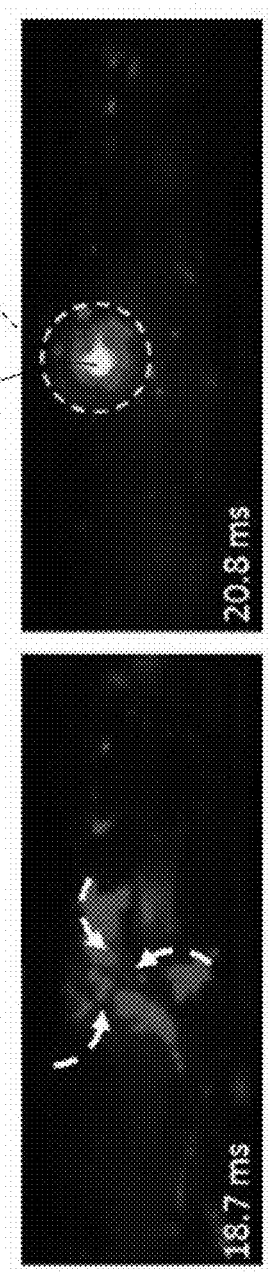
Fig. 4A Fig. 4B Fig. 4C Fig. 4D

ULTRASONIC DEVICE FOR TRANSVERSELY MANIPULATING DRUG DELIVERY CARRIERS AND METHOD USING THE SAME

BACKGROUND

Technical Field

The present disclosure relates to an ultrasonic device. More particularly, the present disclosure relates to an ultrasonic device for transversely manipulating drug delivery carriers and a method using the same.

Description of Related Art

In present medical technology, delivering the drug to a lesion zone without passing the metabolism of the digestive system and the liver to maintain the concentration of the drug in the blood is a concerned research subject. However, it is difficult to deliver the drug to the lesion zone directly.

A drug delivery carrier is any substrate used in the process of drug delivery which serves to improve the selectivity, effectiveness, and/or safety of drug administration. Drug delivery carriers are primarily used to control the release of a drug into systemic circulation. This can be accomplished either by slow release of the drug over a long period of time or by triggered release at the drug's target by some stimulus, such as changes in pH, application of heat, and activation by light. However, the drug delivery carriers still cannot be delivered preciously so as to influence a local concentration of the drug delivery carriers at the lesion zone.

Manipulation of drug delivery carriers, such as microbubbles, cells and droplets, based on acoustic wave has become significant interest in biological and biomedical research due to their non-contact and non-invasive characters. The gas-filled microbubbles are encapsulated by an elastic shell and have great potential applications in drug delivery and targeted imaging. Transportation and trapping of the microbubbles to desired positions can improve the local concentration of the microbubbles in targeted areas and provide more efficient bonding.

One of current methods for manipulating the microbubbles is performed by a standing acoustic wave. The standing acoustic wave has become a powerful and active strategy to levitate or manipulate single or multiple particles and even living animals. However, forming the standing wave pattern has the nature of mandatory and environment dependent, and thus that limits the possibilities to manipulate an object in real applications. Another one of the current methods for manipulating the microbubbles is performed by a single-beam acoustic tweezer with a high frequency of more than 40 MHz. However, the high frequency is not suitable to be applied on the human body.

SUMMARY

The present disclosure provides an ultrasonic device for transversely manipulating drug delivery carriers includes a driving unit and a transducer. The transducer is electrically connected to the driving unit and has a piezoelectric sheet in a curved shape. The piezoelectric sheet includes a plurality of channels, and a phase difference is generated between every two of the channels by the driving unit for producing an acoustic vortex.

The present disclosure further provides a method for transversely manipulating drug delivery carriers, and the method includes the following steps. First, an ultrasonic executing step is performed for producing the acoustic vortex by the ultrasonic device as mentioned above. A focusing step is performed for focusing the drug delivery carriers toward a center of the acoustic vortex, and a manipulating step is then performed for manipulating the drug delivery carriers to a lesion zone.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present disclosure can be more fully understood by reading the following detailed description of the embodiment, with reference made to the accompanying drawings as follows:

FIG. 4A is an image showing microbubbles in a needle hydrophone without applying the acoustic vortex according to Example 1 of the present disclosure;

FIGS. 4B~4D are images showing the microbubbles of FIG. 4A with applying the acoustic vortex;

DETAILED DESCRIPTION

The present disclosure provides an ultrasonic device for transversely manipulating drug delivery carriers and allows collect and manipulation microbubbles in a desired position. The low frequency, appropriate working distance for veins, arteries or a deep tissue of the human body, and single-beam configuration provide superior usefulness compared with the conventional methods particularly in drug delivery applications.

Figure 1A:
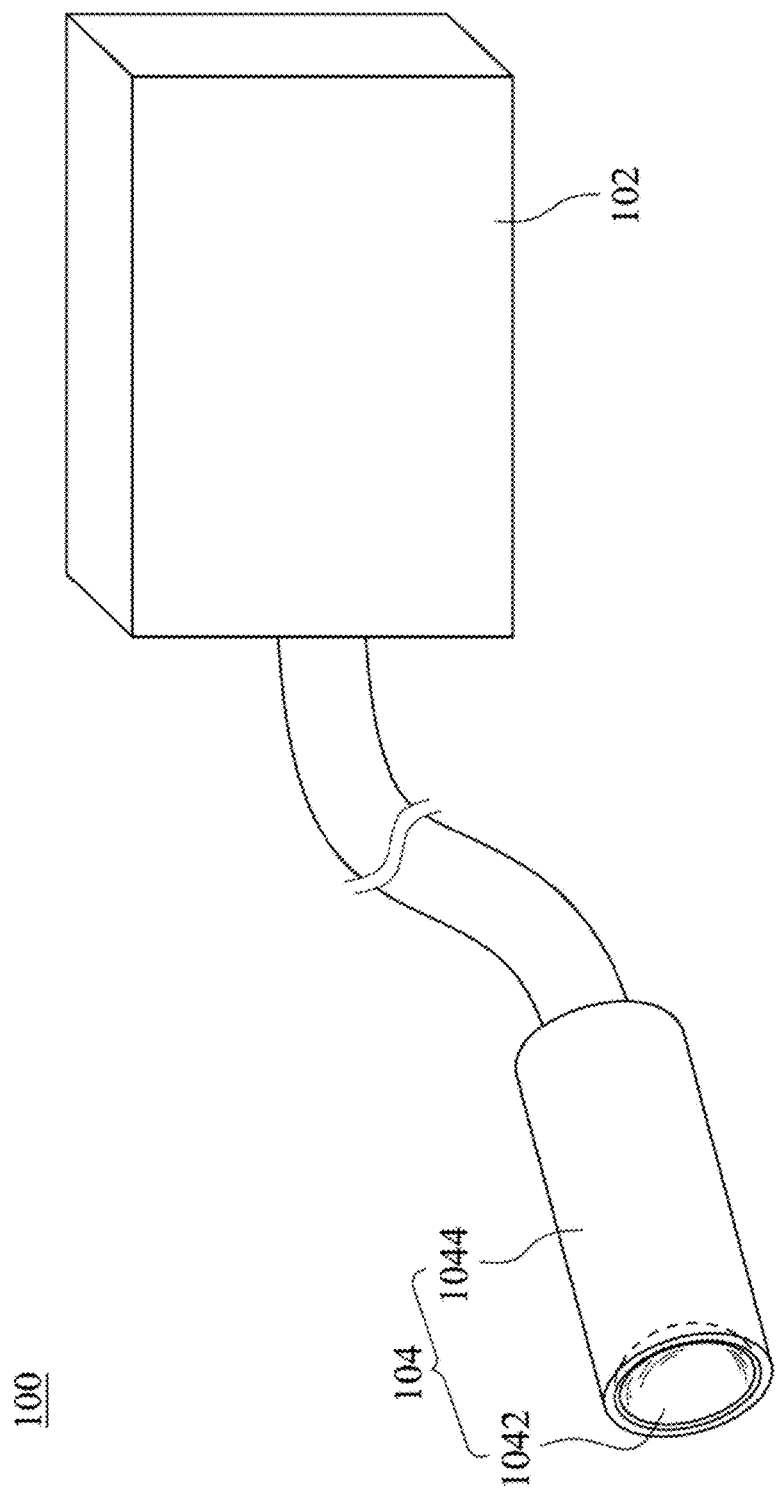
FIG. 1A is a schematic drawing of an ultrasonic device for transversely manipulating drug delivery carriers according to one embodiment of the present disclosure.
Figure 1B:
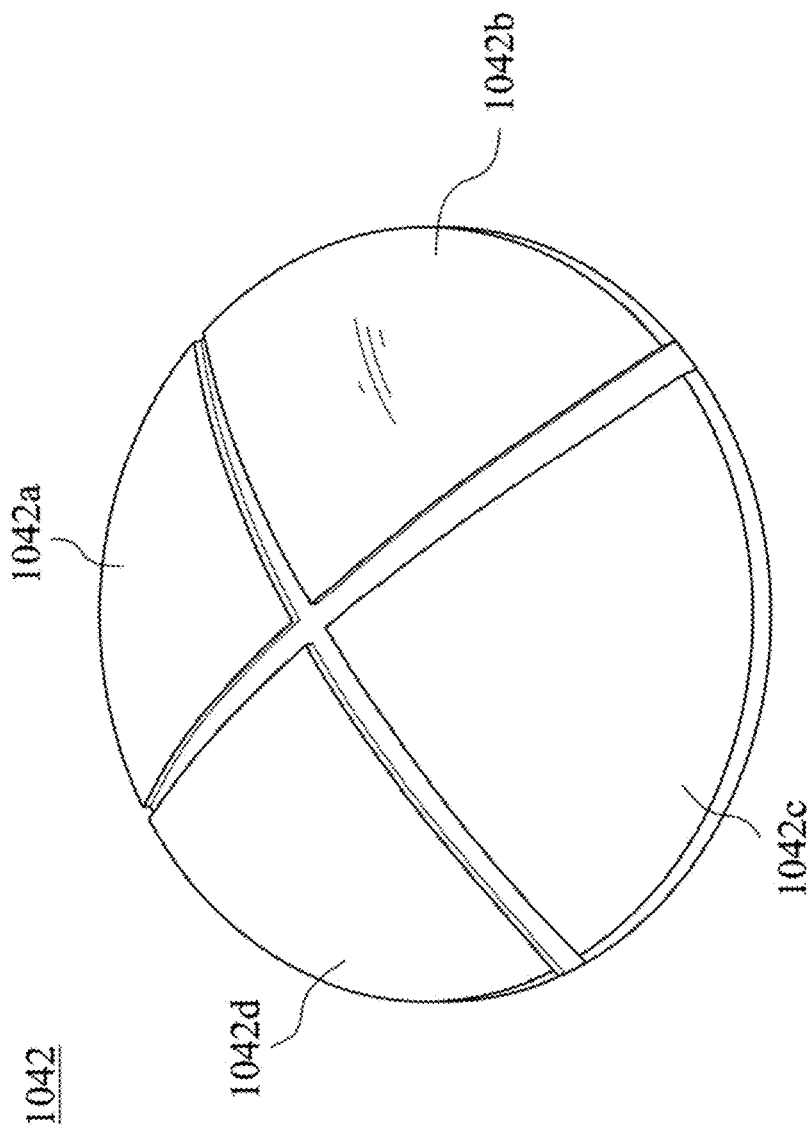
FIG. 1B is a schematic drawing of a piezoelectric sheet according to one embodiment of the present disclosure.

Please refer to FIG. 1A and FIG. 1B. FIG. 1A is a schematic drawing of an ultrasonic device 100 for transversely manipulating drug delivery carriers according to one embodiment of the present disclosure, and FIG. 1B is a schematic drawing of a piezoelectric sheet 1042 according to one embodiment of the present disclosure. As shown in FIG. 1A, the ultrasonic device 100 for transversely manipulating drug delivery carriers at least includes a driving unit 102 and a transducer 104. The transducer 104 is electrically connected to the driving unit 102. Furthermore, the transducer 104 has a piezoelectric sheet 1042, and the piezoelectric sheet 1042 is in a curved shape and includes a plurality of channels (please refer to FIG. 1B). A phase difference is generated between every two of the channels by the driving unit for producing an acoustic vortex (not shown in the figure).

In particular, the driving unit 102 can be a pulse generator. More particularly, the driving unit 102 can be but not limited to a field-programmable gate array (FPGA)-based pulse generator. In addition, a driving signal transmitted by the driving unit 102 can be a square-wave signal or a sine wave signal. Although an amplifier is not shown in the figure, the amplifier can be disposed between the driving unit 102 and the transducer 104 for amplifying the driving signal.

In particular, the transducer 104 can be an array-based transducer. Thus, as shown in FIG. 1B, the piezoelectric sheet 1042 is cut into four adjacent channels, that is, channel 1042a, channel 1042b, channel 1042c and channel 1042d. In addition, the channel 1042a, channel 1042b, channel 1042c and channel 1042d can be obtained by a laser cutting method so as to maintain characteristics of the piezoelectric sheet 1042. However, the present disclosure is not limited thereto. The piezoelectric sheet 1042 also can be cut into eight adjacent channels.

In details, the transducer 104 further includes a case 1044 for sealing the piezoelectric sheet 1042 therein. According to one embodiment of the present disclosure, the piezoelectric sheet 1042 is made of lead zirconate titanate (PZT), and the case 1044 is made of acrylic material. Moreover, the case 1044 can be filled with epoxy, but the present disclosure is not limited thereto.

It is noted that the piezoelectric sheet 1042 has a curvature radius ranged from 10 mm to 100 mm. In details, a focal length of the piezoelectric sheet 1042, that is, the working distance of the transducer 104, is ranged from 10 mm to 100 mm. More particularly, the curvature radius of the piezoelectric sheet 1042 is ranged from 10 mm to 30 mm. Such the working distance of the transducer 104 is short enough to be applied in the veins or arteries of the human body, a micro-electro-mechanical system, or a microscopic scale.

Figure 2A:
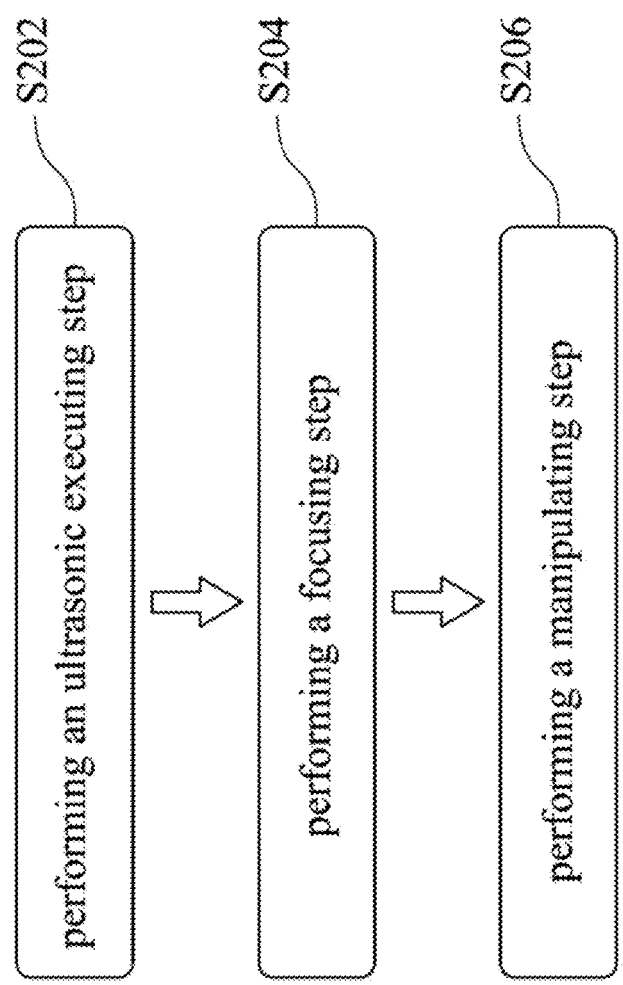
FIG. 2A is a flow chart of a method for transversely manipulating drug delivery carriers according to one embodiment of the present disclosure.
Figure 2B:
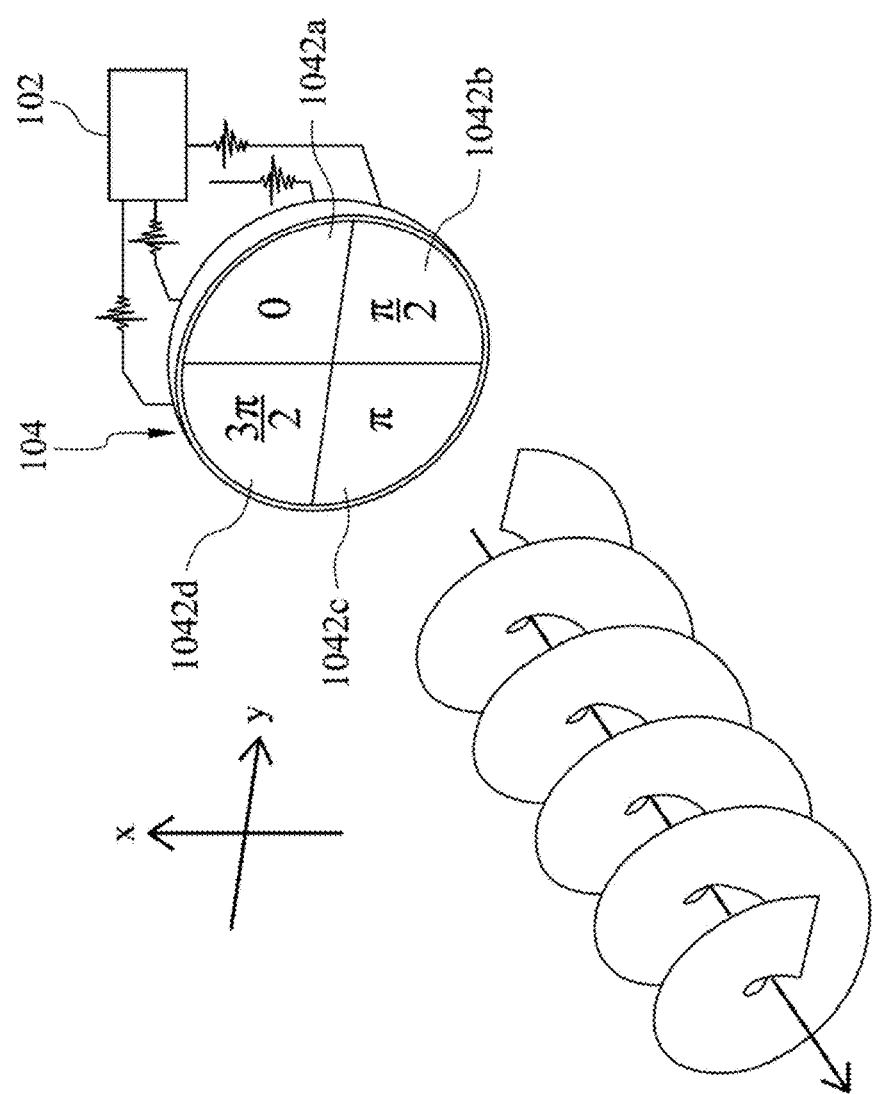
FIG. 2B is a schematic drawing showing an operation mode of the ultrasonic device in FIG. 1A.
Figure 2C:
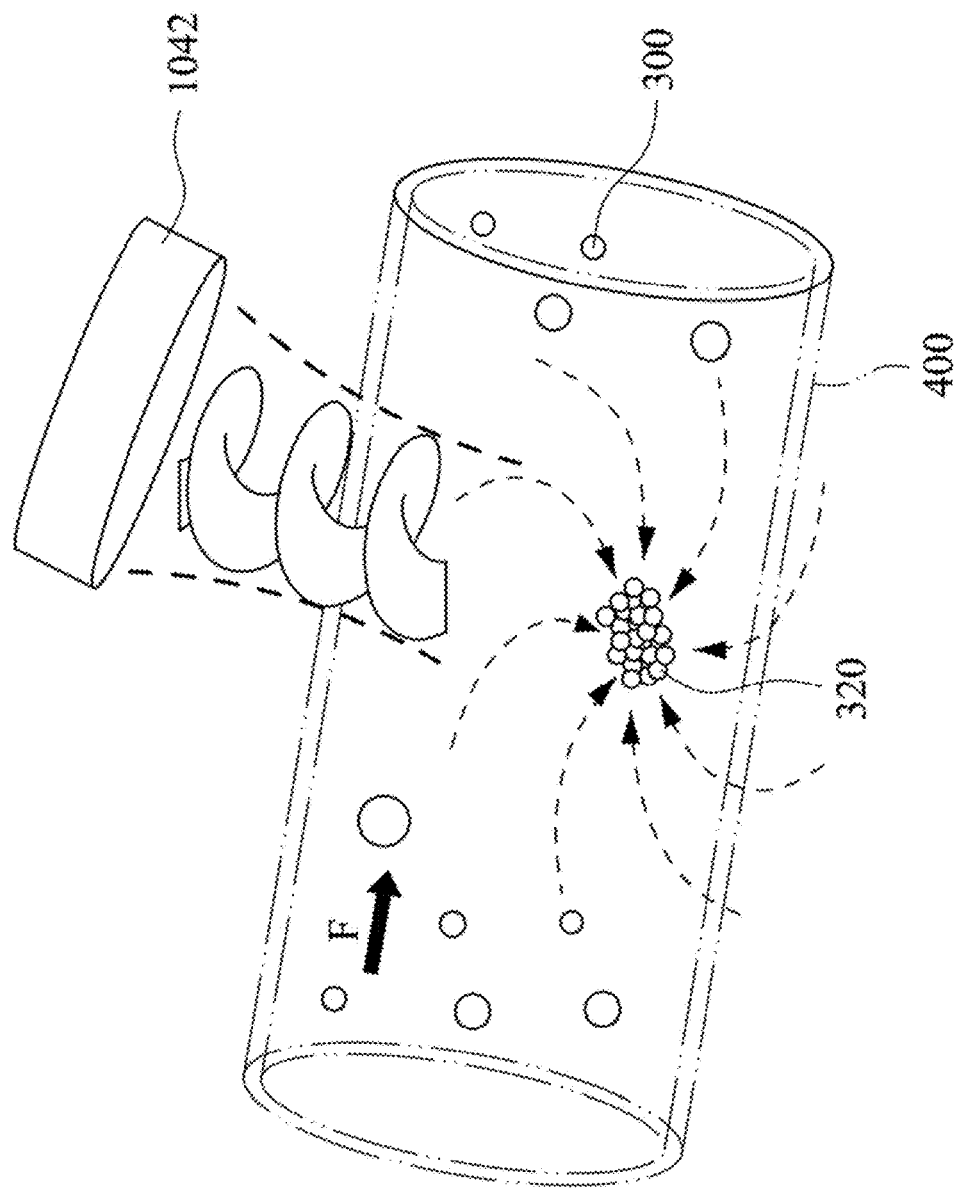
FIG. 2C is a schematic drawing showing the method for transversely manipulating drug delivery carriers of Step S204 in FIG. 2A.

Please refer to FIG. 2A, FIG. 2B and FIG. 2C. FIG. 2A is a flow chart of a method for transversely manipulating drug delivery carriers according to one embodiment of the present disclosure, FIG. 2B is a schematic drawing showing an operation mode of the ultrasonic device 100 in FIG. 1A, and FIG. 2C is a schematic drawing showing the method for transversely manipulating drug delivery carriers of Step S204 in FIG. 2A. As shown in FIG. 2A, the present disclosure further provides a method for transversely manipulating drug delivery carriers, and the method includes Step S202, Step S204 and Step S206.

Step S202 is an ultrasonic executing step. As mentioned above, the transducer 104 of the present disclosure can adopt the piezoelectric sheet 1042 with four channels as shown in FIG. 2B. It is noted that the piezoelectric sheet 1042 of the present disclosure needs to be in the curved shape although it seems a planar sheet in FIG. 2B for further illustration. In Step S202, the piezoelectric sheet 1042 can be driven with $\pi/2$-rad phase difference along the beam axis to produce an acoustic vortex. That is, the phase difference of $\pi/2$ is generated between every two of the channel 1042a, channel 1042b, channel 1042c and channel 1042d. However, the abovementioned phase difference can be ranged from $\pi/8$ to $\pi/2$ and is not limited thereto. Accordingly, each channel could be manually controlled so that the present disclosure has less limitation for application.

Step S204 is a focusing step. As shown in FIG. 2C, for simulating the application in the human body, the drug delivery carriers 300 can be suspended in a vessel phantom 400, such as a vein phantom or an artery phantom, and flow along with a direction F of a fluid filled in the vessel phantom 400. Thus, Step S204 is provided for creating a steep potential distribution in a center of the vortex so as to focus the drug delivery carriers 300 toward the center of the acoustic vortex to form a microbubbles cluster 320.

Step S206 is a manipulating step for manipulating the drug delivery carriers 300 to a lesion zone (not shown in the figure).

In details, Step S202 is performed by the driving unit, preferably a pulse generator, with a frequency ranged from 3 MHz to 20 MHz, preferably from 3 MHz to 5 MHz. Accordingly, such the low frequency is suitable to be applied in the human body. Furthermore, Step S202 is performed by the pulse generator with a duty cycle of 30% or above.

Moreover, the drug delivery carriers of the present disclosure are a plurality of microbubbles. In particular, an average particle size of the microbubbles is ranged from 1 $\mu$m to 200 $\mu$m. Furthermore, each of the microbubbles comprises an ultrasound contrast agent or a drug. It is noted that each of the microbubbles is an elastomer and can generate a cavitation with the acoustic vortex so as to be controlled by a radiation force.

The ultrasonic device for transversely manipulating drug delivery carriers and the method using the same have been described as mentioned above. In the following, Example 1 and example 2 will be further provided to illustrate transmit conditions of the abovementioned ultrasonic device 100, the method using the same, and the effects of the present disclosure in details.

Example 1

In Example 1, the driving unit is a FPGA-based pulse generator a phase shift of $2\pi$. The vortex acoustic field generated is measured at two different observation planes using a 200 $\mu$m needle hydrophone (HG-0085, Onda, Sunnyvale, USA) mounted on a 3-D computer controlled motor system. Herein, the needle hydrophone is used as a vessel phantom, such as a vein phantom or an artery phantom, for simulating the application in the human body. Furthermore, the piezoelectric sheet of the transducer has four channels. More particularly, a curvature radius of the piezoelectric sheet is 20 mm.

In Example 1, each of the microbubbles is used as the drug delivery carrier, respectively, and can be a phospholipid-coated microbubble. More particularly, the microbubbles are fabricated by using the compositions of 1,2-dipalmitoyl-sn-glycero-3-phosphocholine (DPPC), 1,2-distearoyl-sn-glycero-3-phospho-(1'-rac-glycerol) (DSPG), and 1,2-distearoyl-sn-glycero-3-phosphoethanolamine-N-[methoxy(polyethylene glycol)-5000] (DEPE-PEG5000). However, the present disclosure is not limited thereto.

In brief, the center of the acoustic vortex where all phases are perfect destructive interference results from the beam axis so as to form a potential well. In Example 1, the microbubbles are exposed to the acoustic vortex at one fourth the Rayleigh distance (RD/4) from the transducer. When the microbubbles are subjected into a fluid of the needle hydrophone and the vortex acoustic field is applied, the oscillating pressure gradient can couple with the bubble oscillations to produce the radiation force. Thus, each of the microbubbles will be trapped at the potential well and then transported. The motion of each microbubble can be recorded with B-mode imaging using a clinical ultrasound imaging system (model t3000, Terason, USA), however, the present disclosure is not limited thereto. Other transmit parameters of the driving unit are listed in Table 1.

TABLE 1

| Frequency (MHz) | 3 |
| --- | --- |
| Waveform | Sinusoid |
| Pulse duration (cycle) | 1000 |
| Duty cycle (%) | 33 |
| Acoustic pressure (kPa) | 40 |

Figure 3B:
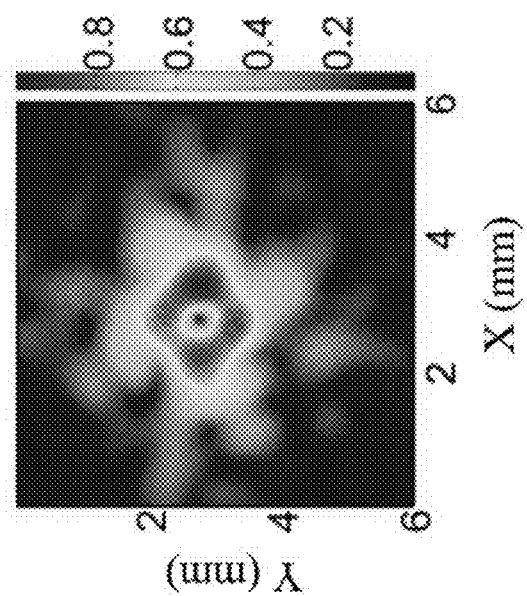
FIG. 3B is a transverse measured result of the vortex acoustic field of FIG. 3A.
Figure 3A:
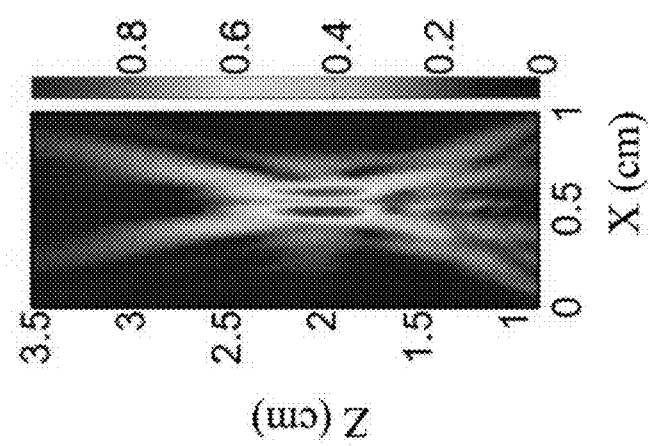
FIG. 3A is an axial measured result of a vortex acoustic filed according to Example 1 of the present disclosure.

Please refer to FIG. 3A and FIG. 3B. FIG. 3A is an axial measured result of a vortex acoustic filed according to Example 1 of the present disclosure, and FIG. 3B is a transverse measured result of the vortex acoustic field of FIG. 3A. As shown in FIG. 3A, the focal length of the vortex acoustic filed is 2 cm. That is, the manipulation of the microbubbles using the ultrasonic device provided in Example 1 has a shorter working distance so as to be applied in the micro-electro-mechanical system or the microscopic scale easily. Furthermore, the acoustic vortex refers to a type of beam having a helicoidal wavefront, and hence the beam has a central dark core H of zero amplitude surrounded by a high intensity ring as shown in FIG. 3B.

Please refer to FIGS. 4A~4D. FIG. 4A is an image showing microbubbles 300 in a needle hydrophone without applying the acoustic vortex according to Example 1 of the present disclosure, and FIGS. 4B~4D are images showing the microbubbles 300 of FIG. 4A with applying the acoustic vortex. As shown in FIG. 4A, the microbubbles 300 are suspended in the fluid of the needle hydrophone and flow along the direction F of the fluid, which has a volume velocity of 0.5 mL/hr, when the ultrasonic device is not applied and the acoustic vortex has not been produced yet. When the ultrasonic device is applied on a target zone T, which is represented by a dotted line, to produce the acoustic vortex, the microbubbles 300 start to swirling toward a center of the acoustic vortex as shown in FIG. 4B and FIG. 4C. Finally, a microbubbles cluster 320 will be formed in the target zone T as shown in FIG. 4D.

Figure 4E:
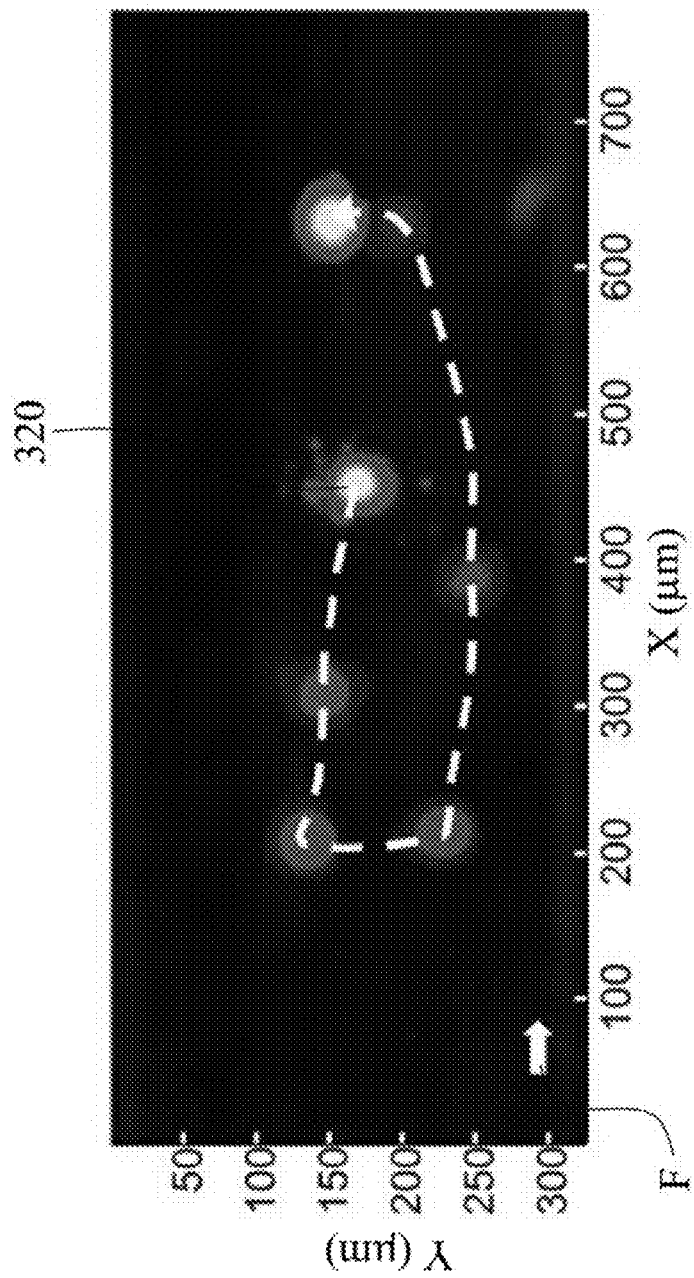
FIG. 4E is an image showing a trajectory of a microbubbles cluster manipulated by the ultrasonic device of FIG. 1A.

Please refer to FIG. 4E, which is an image showing a trajectory of the microbubbles cluster 320 manipulated by the ultrasonic device 100 of FIG. 1A. As shown in FIG. 4E, the microbubbles cluster 320 can be manipulated to move along with the motions of the transducer. That is, the acoustic vortex provides the capability of 2-D particles manipulation.

Figure 5A:
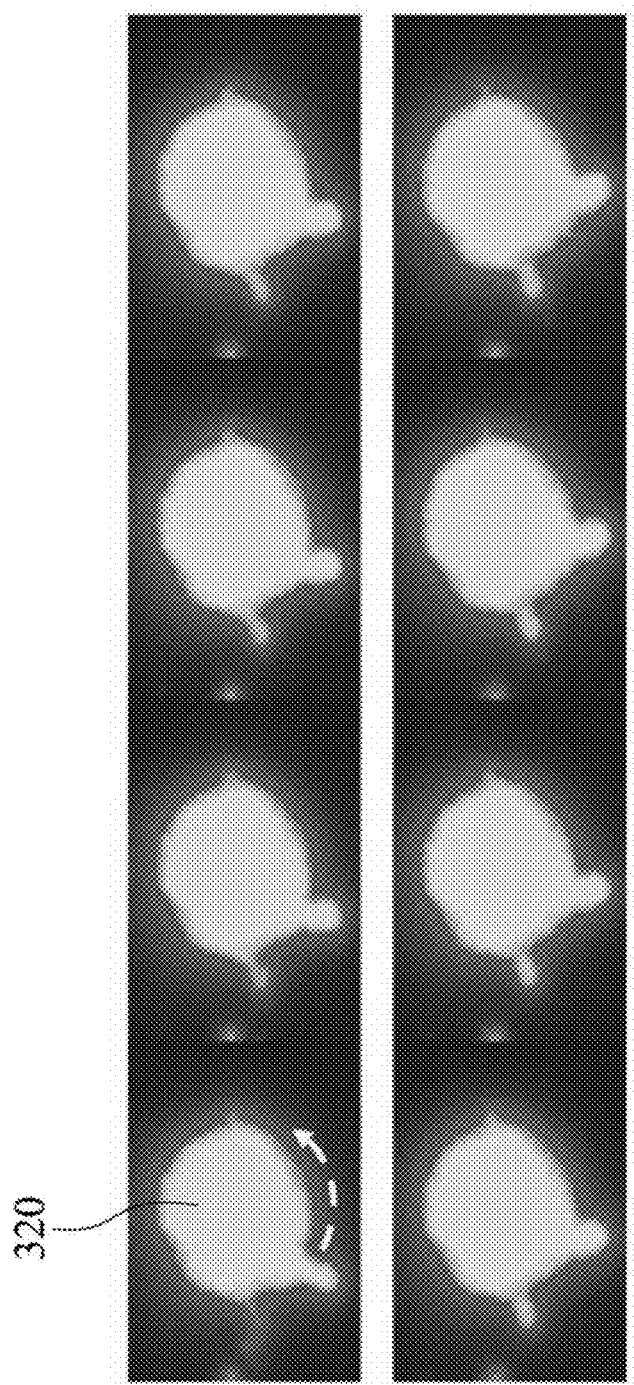
FIG. 5A is an image showing a counterclockwise manipulation of a microbubbles duster.
Figure 5B:
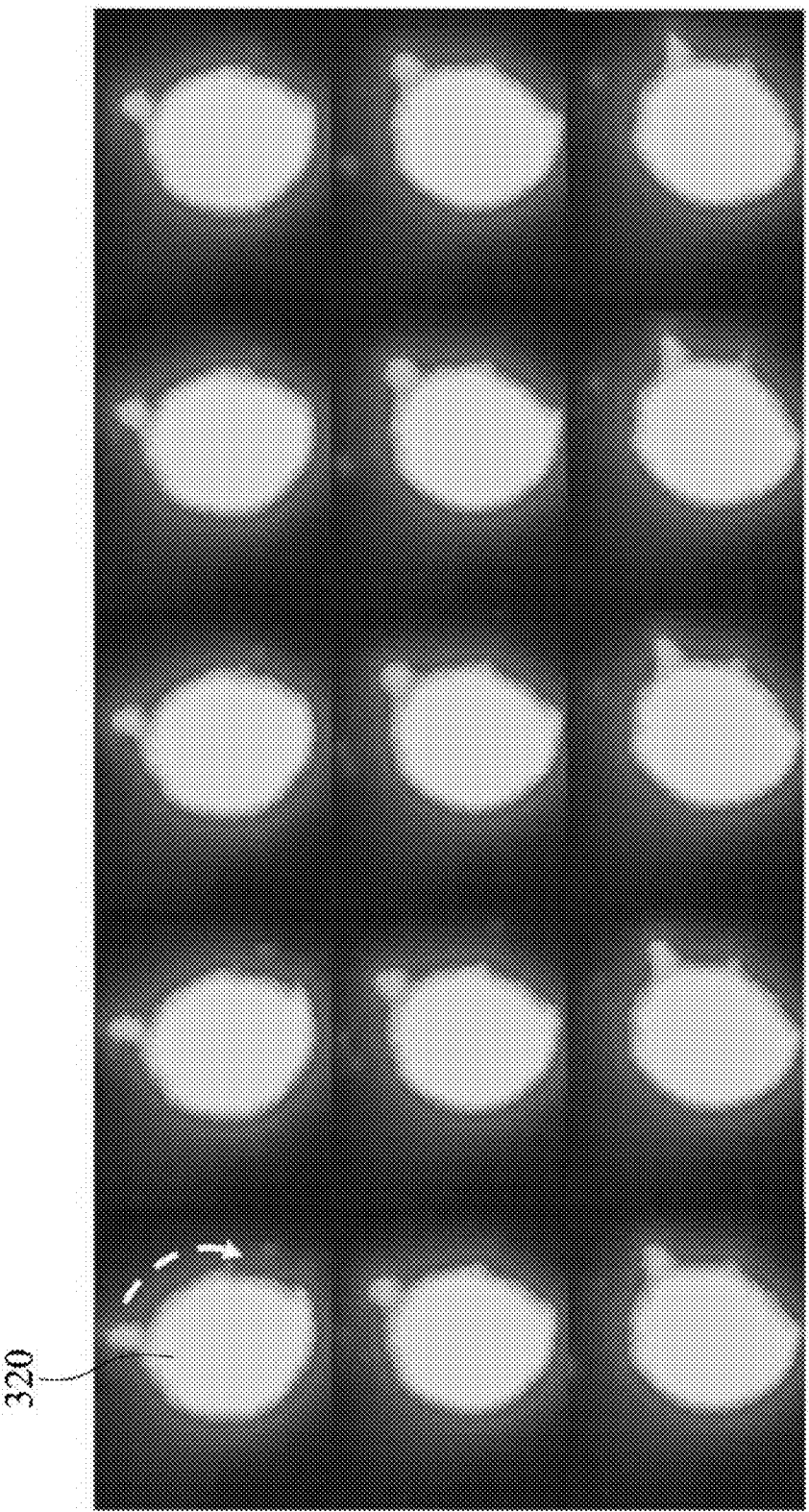
FIG. 5B is an image showing a clockwise manipulation of a microbubbles cluster.

Please further refer to FIG. 5A and FIG. 5B. FIG. 5A is an image showing a counterclockwise manipulation of the microbubbles cluster 320, and FIG. 5B is an image showing a clockwise manipulation of the microbubbles cluster 320. In FIG. 5A, from left to right and from up to down, the microbubbles cluster 320 can be manipulated to perform a counterclockwise rotation. In FIG. 5B, from left to right and from up to down, the microbubbles cluster 320 also can be manipulated to perform a clockwise rotation. That is to say, except for the transportation, the acoustic vortex of the present disclosure also can manipulate the microbubbles duster to rotate.

Example 2

Example 2 is provided for simulating the manipulation of the microbubbles under a high flow rate, for example, the manipulation in the artery. The ultrasonic device and the method for manipulating the drug delivery carriers of Example 2 are similar to Example 1 except the transmit parameters. The transmit parameters are further listed in Table 2.

TABLE 2

| Frequency (MHz) | 3 |
| --- | --- |
| Waveform | Sinusoid |
| Pulse duration (cycle) | 1000 |
| Duty cycle (%) | 99 |
| Acoustic pressure (kPa) | 800 |

Figure 6:
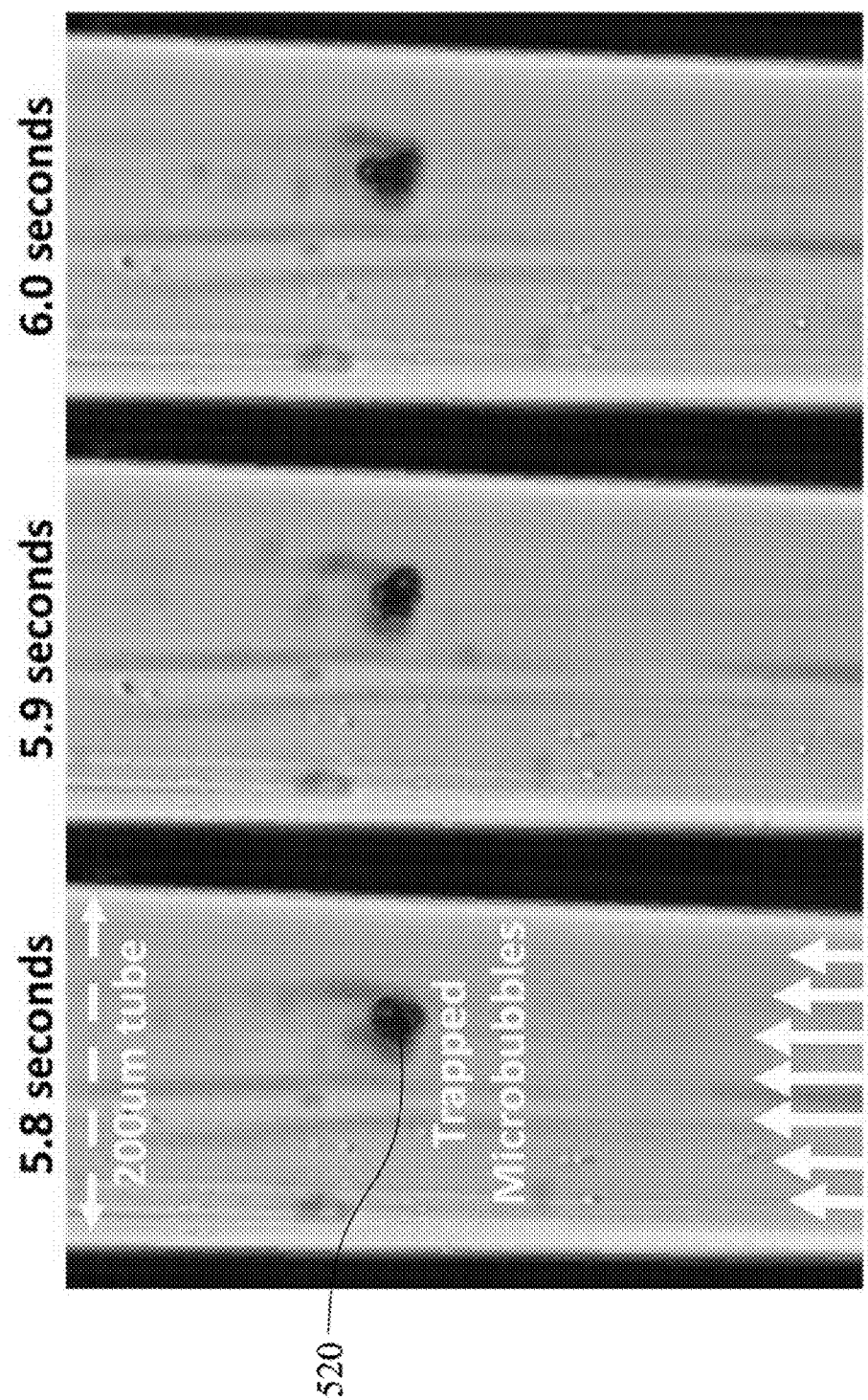
FIG. 6 is an image showing a manipulation of microbubbles in a needle hydrophone with a high flow rate according to Example 2 of the present disclosure.

Please refer to FIG. 6, which is an image showing a manipulation of microbubbles in a needle hydrophone with a high flow rate according to Example 2 of the present disclosure. In Example 2, it is noted that the microbubbles (not shown in the figure) still can be trapped to form a microbubbles duster 520 even though the flow rate of the fluid in the needle hydrophone is 5 mL/hr. That is, the ultrasonic device and the method for manipulating the drug delivery carriers disclosed in the present disclosure can be applied but not limited to the artery, where has a high flow rate of blood, of the human body.

To sum up, the present disclosure provides an ultrasonic device for transversely manipulating drug delivery carriers and allows collect and manipulation microbubbles in a desired position. The low frequency, appropriate working distance for veins, arteries or a deep tissue of the human body, and single-beam configuration provide superior usefulness compared with the conventional methods particularly in drug delivery applications. Moreover, the trapping characteristics may be useful to increase the efficiency of microbubbles accumulation at the lesion zone.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An ultrasonic device for transversely manipulating drug delivery carriers, comprising:
    a driving unit; and
    a transducer electrically connected to the driving unit and having a piezoelectric sheet in a curved shape, wherein the piezoelectric sheet comprises a plurality of channels, a phase difference is generated between every two of the channels by the driving unit, and the phase differences between every two of the channels are circularly aligned for producing an acoustic vortex;
    wherein the acoustic vortex swirls the drug delivery carriers to a center of the acoustic vortex, a potential wall is formed in the center of the acoustic vortex, the drug delivery carriers are trapped in the potential wall and then transported, and the acoustic vortex manipulates the drug delivery carriers to move along a motion of the transducer or manipulates the drug delivery carriers to rotate;

wherein the potential wall is generated in the center of the acoustic vortex where all phases are perfect destructive interference results from a beam axis.

2. The ultrasonic device of claim 1, wherein the piezoelectric sheet has a curvature radius ranged from 10 mm to 100 mm.

3. The ultrasonic device of claim 1, wherein the piezoelectric sheet is made of lead zirconate titanate.

4. The ultrasonic device of claim 1, wherein the transducer further comprises:
   a case provided for sealing the piezoelectric sheet and filled with epoxy.

5. The ultrasonic device of claim 1, wherein the driving unit comprises a pulse generator.

6. The ultrasonic device of claim 1, wherein the drug delivery carriers comprise a plurality of microbubbles.

7. A method for transversely manipulating drug delivery carriers, comprising:
   performing an ultrasonic executing step for producing the acoustic vortex by the ultrasonic device of claim 1, wherein the acoustic vortex is generated by circularly aligned phase differences between every two of the channels;
   performing a focusing step for focusing the drug delivery carriers toward a center of the acoustic vortex, wherein a potential wall is formed in the center of the acoustic vortex, wherein the potential wall is generated in the center of the acoustic vortex where all phases are perfect destructive interference results from a beam axis, and the drug delivery carriers are trapped in the potential wall and then transported; and
   performing a manipulating step for manipulating the drug delivery carriers to a lesion zone, wherein the drug delivery carriers are manipulated to move along a motion of the transducer or manipulated to rotate.

8. The method of claim 7, wherein the piezoelectric sheet of the ultrasonic device has a curvature radius ranged from 10 mm to 100 mm.

9. The method of claim 8, wherein the ultrasonic executing step is performed by a pulse generator with a frequency ranged from 3 MHz to 20 MHz.

10. The method of claim 8, wherein the ultrasonic executing step is performed by a pulse generator with a duty cycle of 30% or above.

11. The method of claim 8, wherein the phase difference is ranged from $\pi/8$ to $\pi/2$.

12. The method of claim 7, wherein the drug delivery carriers comprise a plurality of microbubbles.

13. The method of claim 12, wherein an average particle size of the microbubbles is ranged from 1 μm to 200 μm.

14. The method of claim 12, wherein each of the microbubbles is a phospholipid-coated microbubble.

15. The method of claim 12, wherein each of the microbubbles comprises an ultrasound contrast agent or a drug.

* * * * *